(12) United States Patent
Blackwell et al.

(10) Patent No.: US 8,721,967 B2
(45) Date of Patent: May 13, 2014

(54) APPARATUS FOR TESTING A LIQUID SPECIMEN

(75) Inventors: Oliver Blackwell, Bridgetown (GB); David William Berger, Barnstaple (GB)

(73) Assignee: Berger Blackwell Devices Limited, Somerset (GB)

( * ) Notice: Subject to any disclaimer, the term of this patent is extended or adjusted under 35 U.S.C. 154(b) by 0 days.

(21) Appl. No.: 13/261,538

(22) PCT Filed: Jun. 14, 2011

(86) PCT No.: PCT/GB2011/000887
§ 371 (c)(1),
(2), (4) Date: Dec. 11, 2012

(87) PCT Pub. No.: WO2011/157981
PCT Pub. Date: Dec. 22, 2011

(65) Prior Publication Data
US 2013/0089474 A1   Apr. 11, 2013

(30) Foreign Application Priority Data
Jun. 15, 2010  (GB) .................................. 1009997.6

(51) Int. Cl.
*G01N 33/00* (2006.01)
(52) U.S. Cl.
USPC .......... 422/68.1; 422/500; 422/501; 422/560; 422/561
(58) Field of Classification Search
USPC ..................... 422/68.1, 500, 501, 560, 561
See application file for complete search history.

(56) References Cited

U.S. PATENT DOCUMENTS

| 5,595,187 | A  | * | 1/1997 | Davis ............................ 600/584 |
| 7,458,942 | B2 | * | 12/2008 | Bohannon et al. ............ 600/584 |
| 7,666,148 | B1 |   | 2/2010 | Caillouette |
| 8,491,852 | B2 | * | 7/2013 | Cullen et al. .................. 422/430 |
| 8,506,901 | B2 | * | 8/2013 | Chen et al. .................... 422/402 |
| 2009/0299161 | A1 | * | 12/2009 | Cullen et al. ................. 600/345 |

FOREIGN PATENT DOCUMENTS

| WO | WO 97/35512 | 10/1997 |
| WO | WO 98/38917 | 9/1998 |
| WO | WO 2005/050168 | 6/2005 |

* cited by examiner

*Primary Examiner* — Sam P Siefke
(74) *Attorney, Agent, or Firm* — Iandiorio Teska & Coleman LLP (57) ABSTRACT

Apparatus (2) for testing a liquid specimen, which apparatus (2) comprises a container (4) for the liquid specimen, a response chart (6) which is operable in response to contact with the liquid specimen, and a result chart (8) for use with the response chart (6), and the apparatus (2) being such that: (i) the container (4) comprises a body portion (10), a lid (12), a test chamber (14), and openable means (16) which is adapted to be broken in order to allow the liquid specimen to pass from the body portion (10) into the test chamber (14); (ii) the response chart (6) comprises response portions (18) which are contacted by the liquid specimen, which become differently colored to indicate different characteristics present in the liquid specimen, and which are read at predetermined time intervals; (iii) the result chart (8) comprises result sectors (22), each result sector (22) is for indicating the result of a different test for the liquid specimen, and each result sector (22) has a plurality of differently colored result portions (24), and the different colors of the result portions (24) in each result sector (22) indicate different degrees of result for the test afforded by the result sector (22); (iv) the response chart (6) is inside the container (4); and (v) the result chart (6) is mounted on the outside of the container (4).

14 Claims, 14 Drawing Sheets

APPARATUS FOR TESTING A LIQUID SPECIMEN

This invention relates to apparatus for testing a liquid specimen.

Apparatus for testing a liquid specimen in the form of urine is well known. The testing of urine by the use of a dipstick is one of the most common medical diagnostic tests, and it is carried out many times a day in medical practices, clinics and hospitals around the world. The testing of the urine is essential in the diagnosis of urinary tract infections, for screening for protein and blood in the urine, and for the diagnosis of many other conditions.

The standard way in which the urine is tested with a dipstick involves a patient filling a container with urine, and then handing the container to an authorised person such for example as a nurse, a technician or a doctor. The authorised person puts on gloves, takes the container to a sink and a work surface, and unscrews a lid of the container. The authorised person then unscrews the lid from a container of urine analysis test strips, the person extracts one of the test strips, and briefly dips it into the urine in the container, wiping off excess urine on the rim of the container. The dipstick has response portions which are contacted by the liquid specimen, which become differently coloured to indicate different characteristics present in the urine, and which are read at predetermined time periods. The response portions are read against a result chart at predetermined time intervals of up to two minutes. At the end of the procedure, the urine is discarded, the container is then thrown away, the gloves are removed and also discarded, and the authorised operator washes their hands. This procedure take a minimum of three minutes to perform effectively, and it is awkward with a number of steps. More often than not, the procedure is performed without accurate timing. Also, the procedure is performed such that it exposes the operator and the environment to the risk of contamination by the urine. Similar problems exist with the testing of other liquid specimens.

U.S. Pat. No. 5,119,830 discloses apparatus which is for testing a liquid specimen, and which attempts to overcome the above mentioned problems. However, the apparatus disclosed in the USA patent itself presents problems in that it is not easy to read the results obtained from the apparatus. More specifically, the apparatus uses a chemical test strip which includes response portions which are set out in a straight line. It is difficult to match visually these response portions with precalibrated indicator markings located beside the response portions. Also, the pre-calibrated indicator markings are small and not easy to read.

It is an aim of the present invention to obviate or reduce the above mentioned problems.

Accordingly, the present invention provides apparatus for testing a liquid specimen, which apparatus comprises a container for the liquid specimen, a response chart which is operable in response to contact with the liquid specimen, and a result chart for use with the response chart, and the apparatus being such that (i) the container comprises a body portion, a lid, a test chamber, and openable means which is adapted to be opened in order to allow the liquid specimen to pass from the body portion into the test chamber;

(ii) the response chart comprises response portions which are contacted by the liquid specimen, which become differently coloured to indicate different characteristics present in the liquid specimen, and which are read at predetermined time intervals;

(iii) the result chart comprises result sectors, each result sector is for indicating the result of a different test for the liquid specimen, and each result sector has a plurality of differently coloured result portions, and the different colours of the result portions in each result sector indicate different degrees of result for the test afforded by the result sector;

(iv) the response chart is inside the container;

(v) the result chart is outside of the container; and (vi) the result chart has an aperture which receives a top part of the container, and a peripheral portion which extends transversely outwardly beyond the container and which contains the result sectors.

The apparatus of the present invention may be used for testing a wide variety of liquid specimens. Usually the liquid specimens will be body fluid liquid specimens but other liquid specimens may be tested. Where the liquid specimens are body fluid liquid specimens, then the liquid specimens may be urine, blood or spinal fluid.

The apparatus may include aligning means for aligning one of the result sectors with one of the response portions such that each one of the result sectors has its own one of the response portions.

The apparatus may include a time band which operates consequent upon contact with the liquid specimen to move between the response portions such as to reach each one of the response portions in that predetermined time interval which is required for that response portion and thereby to indicate the correct time to look at that response portion. More than one of the response portions may have the same predetermined time interval, for example where four of the response portions may have to be read at the same time. The time band may be a chromatographic time band. Other types of time band may be employed. Usually, the time band will move in a circle between the response portions on the response chart. The time band may move in a non-circular manner if desired so that, for example the time band could move in a zig-zag manner. The time band, for example the chromatographic time band, may move in any shaped route providing it reaches the response portions in the required predetermined time interval.

The response chart may be inside the container such that the response chart is on the inside of the container. The response chart may be positioned elsewhere on the inside of the container if desired. Sealing of the response chart from the liquid specimen until the openable means is opened not only protects the response chart from the liquid, but it also enables the chemical reagents on the response chart to be protected from the atmosphere, for example from moisture in the atmosphere which might adversely affect the chemical reagents, or from the ultraviolet light. The protection from atmospheric moisture avoids the need to use water absorbents such for example as silica gel but they may be used if desired.

The response portions may be arranged in any shape, for example a circle. The response portions are preferably arranged in a circle around the periphery of the lid of the container. However, alternatively, the response portions may be arranged in a circle inwardly of the periphery of the lid of the container, or elsewhere as may be desired. The apparatus may be one in, which the response portions are arranged in a circle, and in which the result sectors are arranged in a circle and they extend radially outwardly with respect to the aperture.

The result chart may be on the outside of the container by being mounted on the outside of the container. The result chart may alternatively be on the outside of the container by being held on the outside of the container by a person conducting the testing of the liquid specimen. The result chart may alternatively be on the outside of the container by the use of other positioning means.

The apparatus may be one in which the result chart is mounted on the outside of the container by releasable securing means. The releasable securing means may comprise an aperture in the result chart which fits over an upstanding portion of the container. The upstanding portion of the container may be part of the lid. Other types of releasable securing means may be employed. If desired, the result chart may simply rest on the outside of the container, in which case there will be no need for any securing means.

The releasable securing means advantageously secures the result chart at a position which is level with or below the level of the response chart, whereby reading of the result chart is facilitated and whereby the result chart does not block light for reading of the response chart. If desired, the result chart may be at a position which is higher than the level of the response chart.

The result chart may be a transparent result chart, whereby the transparent result chart does not block light for reading of the response chart. If desired, the result chart may be non-transparent.

The apparatus may be one in which the aligning means comprises a first part on the result chart and a second part on the container.

The first part may be a marking on the result chart, and the second part may be a formation on the container. The marking on the result chart may be a visual marking such for example as a visual notch, line or arrowhead.

Alternatively, the first part may be a notch on the result chart, and the second part may be a protuberance which is on the container and which locates in the notch.

Alternatively, the first part may be a marking on the result chart, and the second part may be a marking on the container. The marking on the result chart and/or the marking on the container may be a visual marking such for example as a visual notch, line or arrowhead.

Alternatively, the first part may be an oval aperture in the result chart, and the second part may be an oval upstanding portion of the container.

The response chart and/or the result chart may include time markings giving specific time-reading periods. Thus, for example, the time markings may be such that they indicate the start of the relevant time-reading periods, a thirty second time period, a forty second time period, a sixty second time period, and a two minute time period. Each time period may be that required for its response portion to react to the liquid specimen. More than one of the response portions may have the same time marking.

The response portions in the response chart may be rectangles. The response portions may be of other shapes if desired so that, for example, the response portions may be squares, circles, triangles or stars.

The result portions in the result chart may be ring segments. Other shapes for the result portions may be employed so that, for example, the result portions may be circles, squares, rectangles, triangles or stars. Because the ring segment shapes are curved, they are able to form a circular layout.

The apparatus may be one in which the response portions in the response chart are such that they each comprise a first area which is in contact with the lid, and a second area which is not in contact with the lid. The contacting of the first area of the response portions with the lid may be advantageous where the liquid specimen in the container tends to cause misting, which may obscure the response portions. By having the first area which is in contact with the lid, misting cannot occur because there is no gap. The liquid specimen just contacts the second area of the response portions and travels, for example is absorbed or soaks, to the first area. The response portions may each be a piece of paper which is impregnated with an appropriate chemical. The piece of paper may be, for example, only about 0.8 mm thick. Thicker or thinner values may be employed. The top of each response portion touches the underside of the lid. The underside and outer edges of the response portion are not in contact with the lid and they are exposed as an exposed edge which is able to be contacted by the liquid specimen.

The apparatus may be one in which each result portion in the result chart has a window portion through which the relevant response portions of the response chart can be viewed if the result chart is moved over the response chart, thereby to facilitate accurate colour matching of a response portion with its result portion. The use of the window portions is advantageous in enabling adjacent viewing of a response portion with its relevant result portion in its result sector.

The apparatus may include light-preventing means for preventing light from prematurely reaching the response chart. This ensures that any light-sensitive chemical reagents employed in the response portions of the response chart are not adversely affected by light, even if they are light-sensitive. The light-preventing means may be a cover which is positioned over the response chart. Alternatively, the light-preventing means may be the lid. Alternatively, the light-preventing means may be a foil. Other types of light-preventing means may be employed. The light-preventing means will normally be removed for the performance of the test. Advantageously, the light-preventing means is constructed such that it appears that only the authorised person conducting the test should remove the light-preventing means. This may be effected by the provision of a removal formation that needs relative positioning by the authorised person before the light-preventing means is able to be removed. The removal formation may be a formation for mechanical interaction and/or a formation for visual interaction. The light-preventing means may be the removable formation.

The apparatus may include tamper-evident means for indicating if the light-preventing means has been damaged. The tamper-evident means may be a seal or other device. If the tamper-evident means indicates that the light-preventing means has been damaged, then a person operating the apparatus will be warned that the response portions may have been damaged by light, for example ultraviolet light.

The openable means may be a membrane which is opened by being broken. Alternatively, the openable means may be a foil. The foil may be a foil which excludes ultraviolet light. Other types of openable means may be employed. Thus, for example, the openable means may be a removable obturator such as a bung or disc, or it may be a flexible flap which pivots with respect to an opening to open and close the opening. The flexible flap may be made of a flexible plastics material. Usually, the opening of the openable means will be permanent, but the opening may be temporary if desired.

The apparatus may include a pin for piercing the openable means. The pin is preferably located in the lid. Simple depression of the lid can then cause the pin to pierce the openable means. Opening formations other than a pin may be employed.

Embodiments of the invention will now be described solely by way of example and with reference to the accompanying drawings in which.

Referring to FIGS. 1-7, there is shown first apparatus 2 for testing a liquid specimen.

The apparatus 2 comprises a container 4 for the liquid specimen. A response chart 6 is operable in response to contact with the liquid specimen. A result chart 8 is provided for use with the response chart 6.

The apparatus 2 is such that the container 4 comprises a body portion 10, a lid 12, a test chamber 14, and openable means 16 which is adapted to be opened in order to allow some of the liquid specimen to pass from the body portion 10 into the test chamber 14.

The response chart 6 comprises response portions 18 which are arranged in a circle. The response portions 18 are contacted by the liquid specimen. They become differently coloured to indicate different characteristics present in the liquid specimen, and they are read at predetermined time intervals.

The apparatus 2 also comprises a chromatographic time band 20 which operates consequent upon contact with the liquid specimen to move between the response portions 18 such as to reach each one of the response portions 18 in that predetermined time interval which is required for that response portion 18, and thereby to indicate the correct time to look at that response portion 18.

The result chart 8 comprises result sectors 22 which are arranged in a circle such that in use each result sector 22 is aligned with one of the response portions 18 and extends radially outwardly with respect to that response portion 18.

Each result sector 22 is for indicating the result of a different test for the liquid specimen. Each result sector 22 has a plurality of differently coloured result portions 24. The different colours of the result portions 24 in each result sector 22 indicate different degrees of result for the test afforded by the result sector 22. The apparatus 2 is for testing a liquid specimen in the form of urine. The response, chart 6 is on the lid 12 of the container 4. The response portions 18 are arranged in a circle around the periphery of the lid 12 of the container 4.

Figure 1:
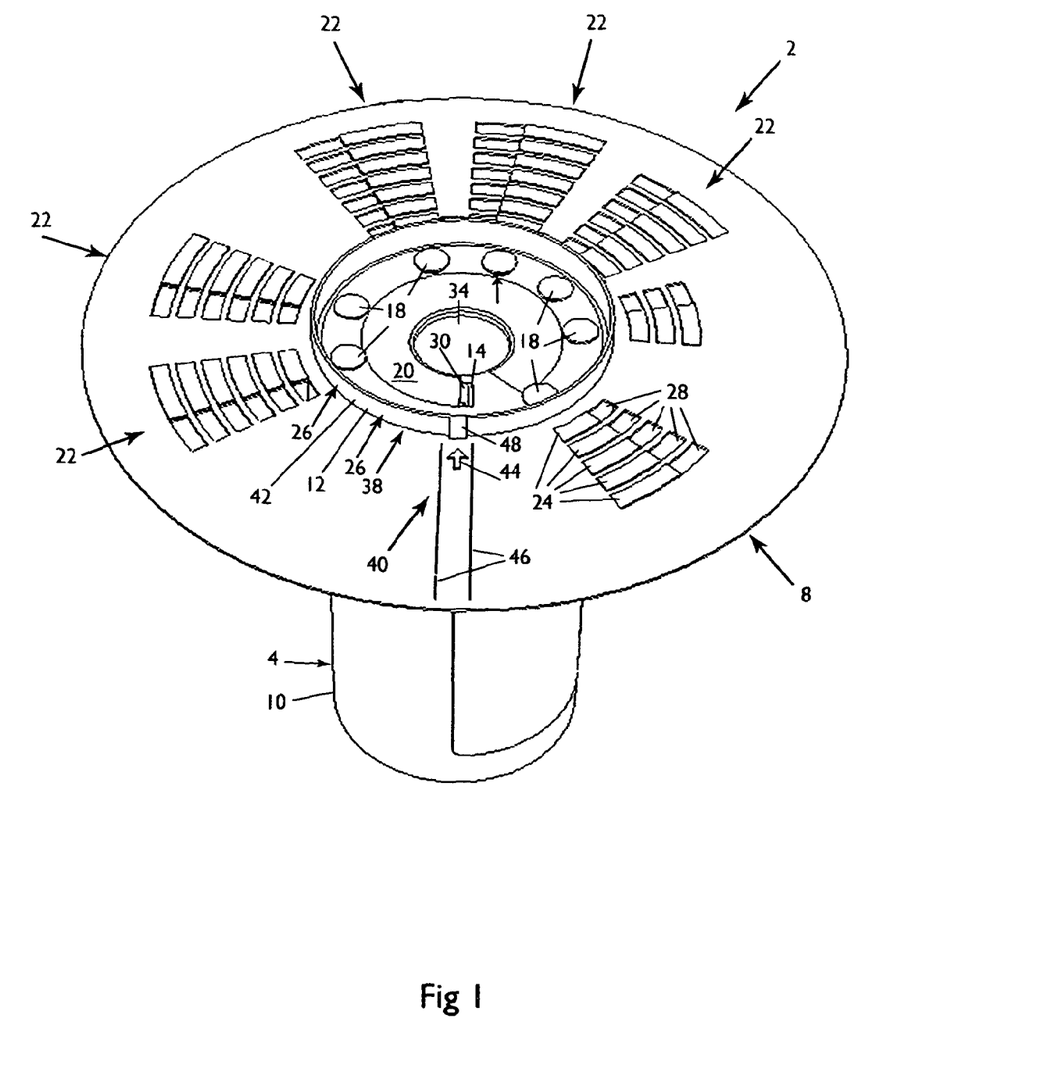
FIG. 1 is an isometric view from above and one side of first apparatus for testing a liquid specimen.
Figure 2:
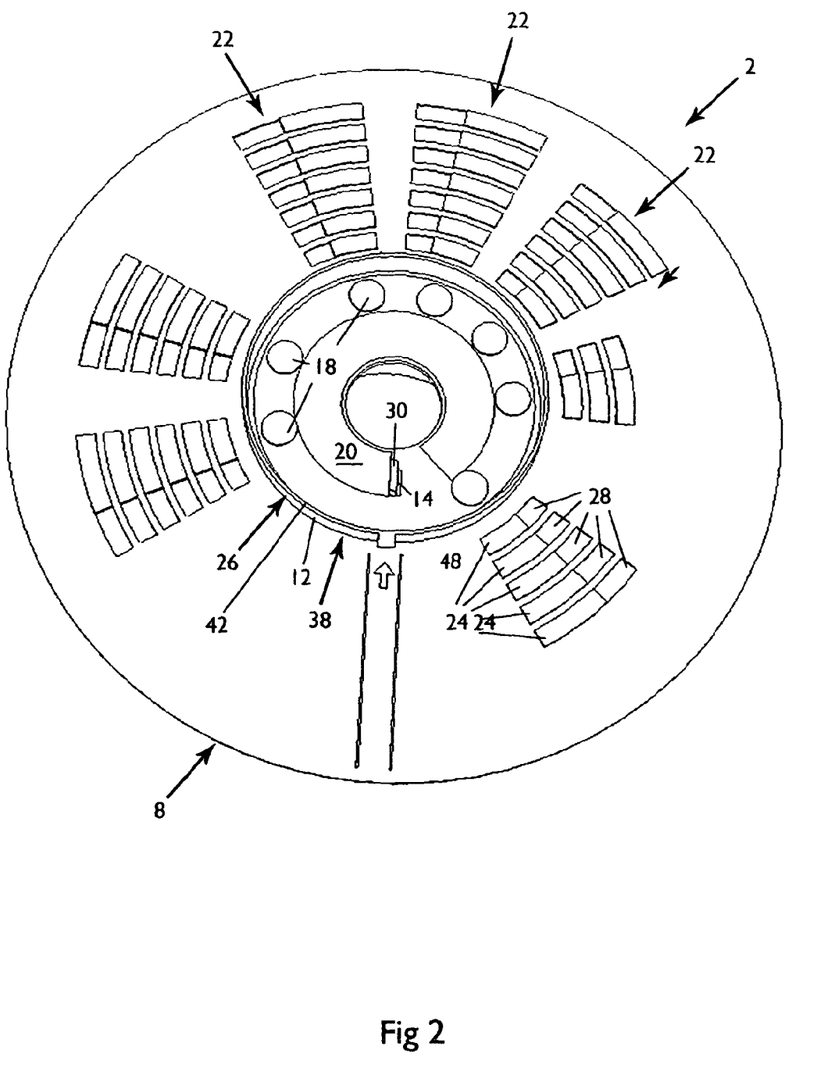
FIG. 2 is a top plan view of the apparatus as shown in FIG. 1.
Figure 3:
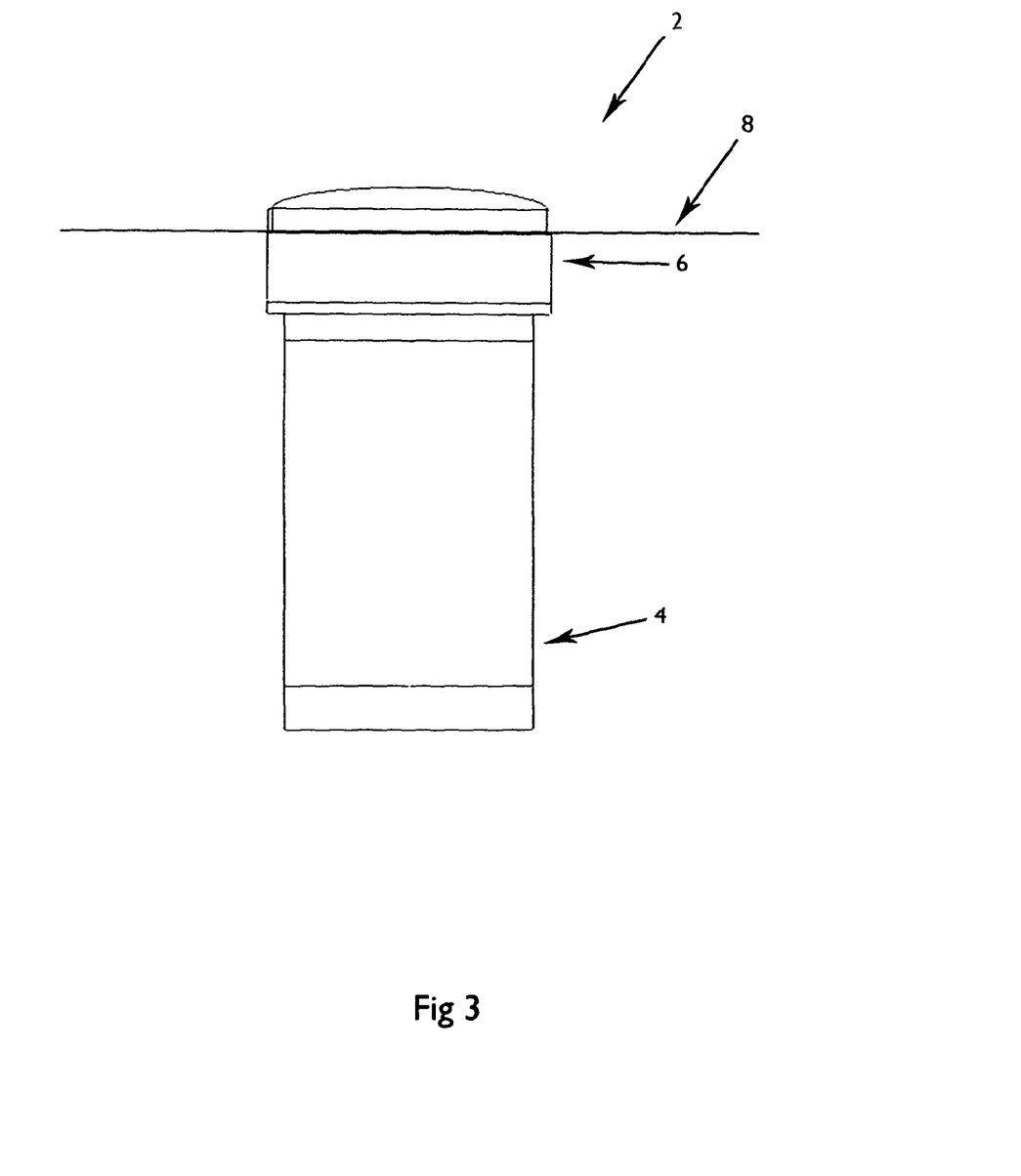
FIG. 3 is a side view of the apparatus as shown in FIG. 1.
Figure 4:
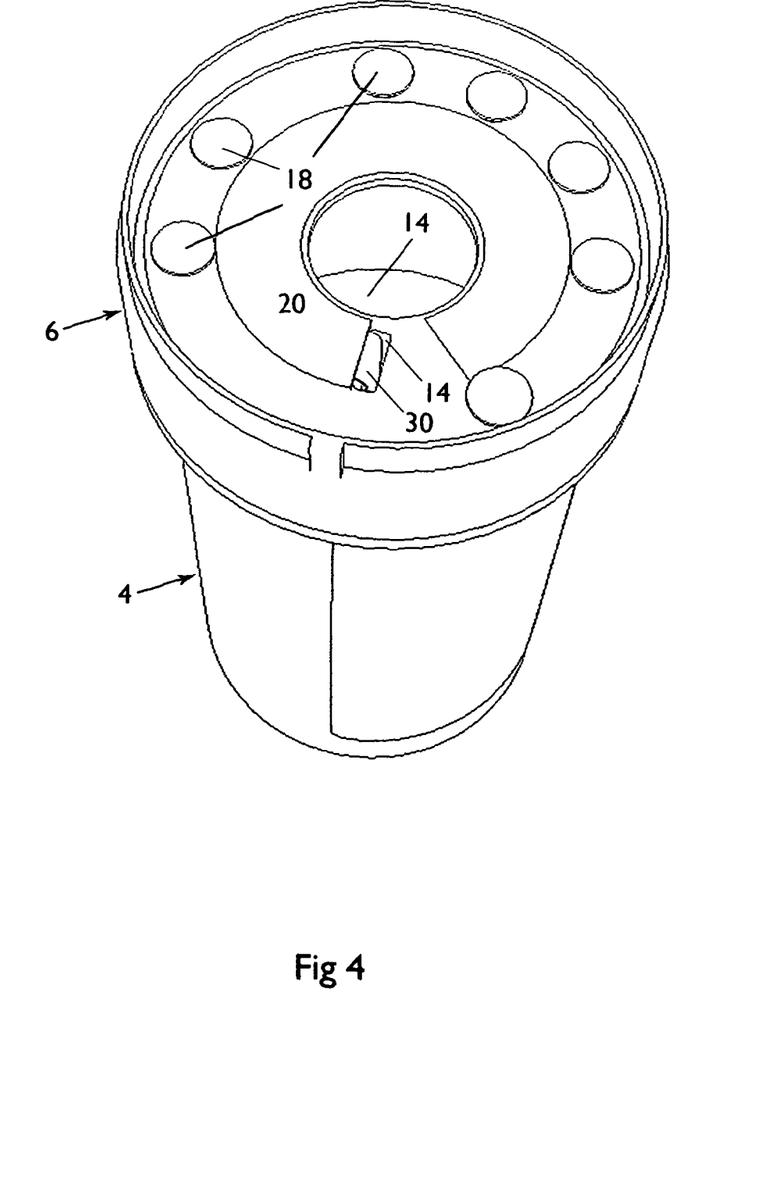
FIG. 4 is an isometric view from above and one side of a container forming part of the apparatus shown in FIG. 1.
Figure 5:
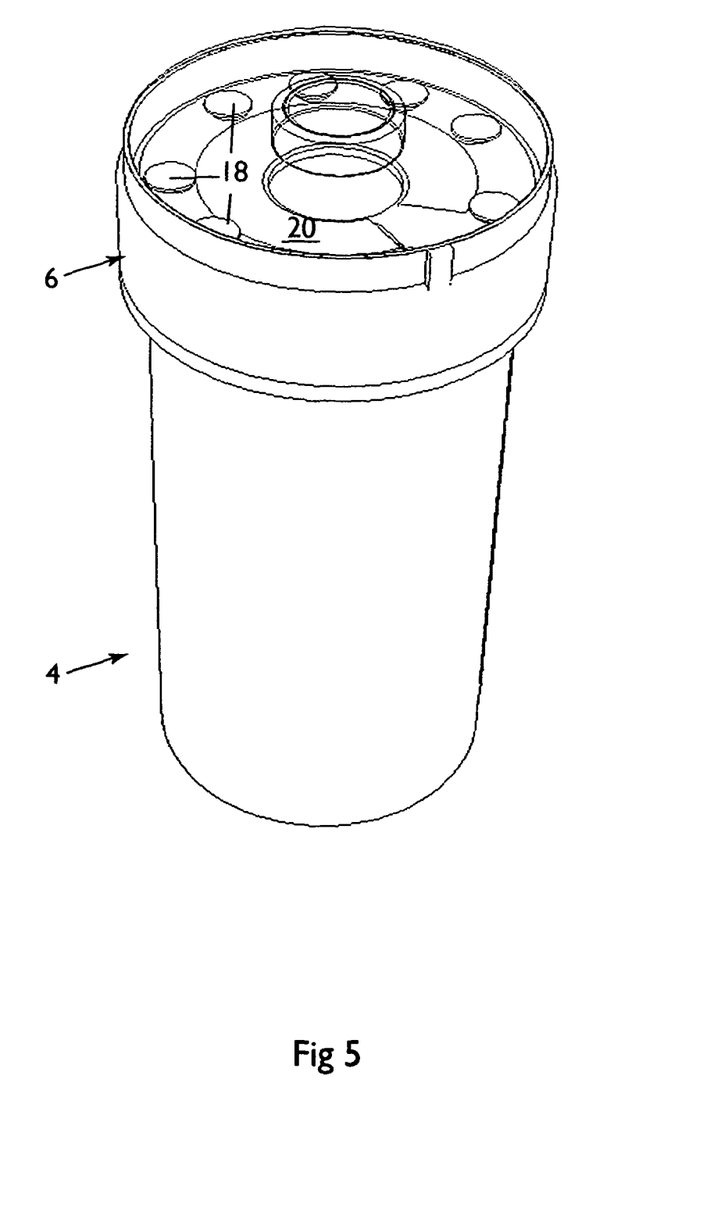
FIG. 5 is another view of the container as shown in FIG. 4.

The result chart 8 fits onto the lid 12 of the container 4 during reading of the result chart 8 in order to obtain a test result from the liquid specimen. More specifically, the result chart 8 has a central aperture 26 for receiving the lid 12 of the container 4 such that the result sectors 22 on the result chart 8 are able to be aligned with the response portions 18 on the response chart 6.

The chromatographic time band 20 moves in a circle between the response portions 18 on the response chart 6. The response chart 6 includes time markings giving predetermined time periods for each response portion 18 in the response chart 6. The response portions have a start period, and then they are twenty seconds, forty seconds, sixty seconds, and two minutes.

Each result portion 24 in the result chart 8 has a window portion 28 through which the relevant response portion 18 of the response chart 6 can be viewed if the result chart 8 is moved over the response chart 6. This facilitates accurate colour matching of the response portion 18 with its result portion 24 because the response portion 18 and the result portion 24 are able to be viewed side by side. The result chart 8 may also include time markings (not shown).

The chromatographic time band 20 is formed by a waterproof layer extending over a circular reagent strip 30. One end of the circular reagent strip 30 dips into the test chamber 14 as can be appreciated from FIG. 1.

Figure 6:
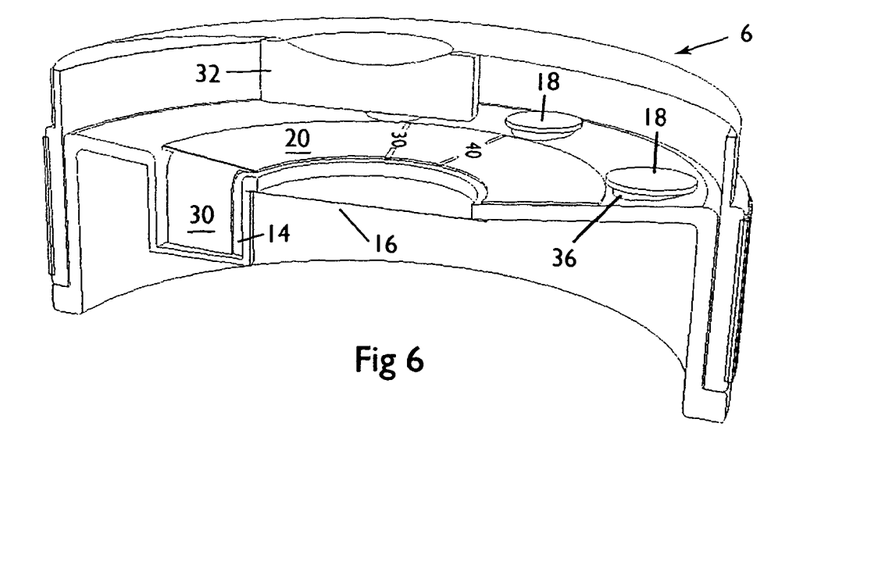
FIG. 6 is a section through a first part of a lid of the container shown in FIGS. 4 and 5.
Figure 7:
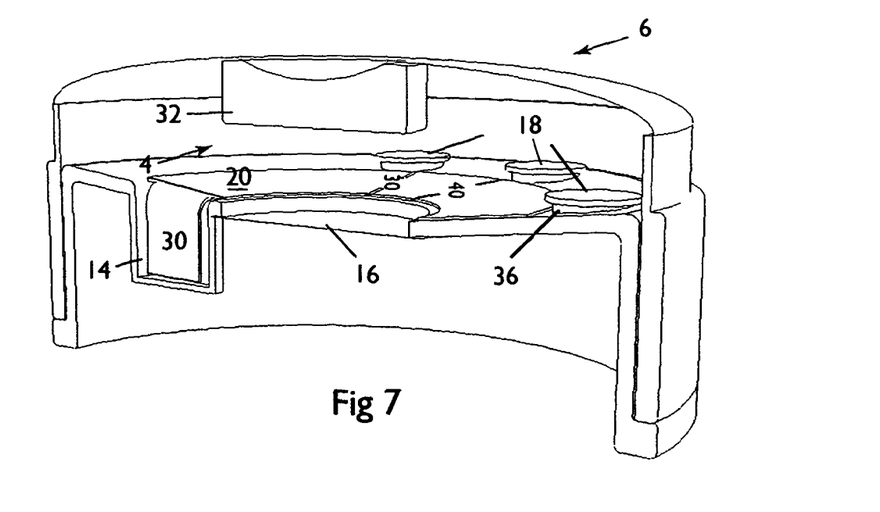
FIG. 7 is another sectional view like FIG. 6 but rotated slightly with respect to FIG. 6.

The openable means 16 is a membrane. The apparatus 2 includes a pin 32 for piercing the openable means 16. The pin 32 is in the lid 12 of the container 4. It is simply necessary to press an appropriate part of the lid 12 in order to cause the pin 32 to break the openable means 16.

The apparatus 2 advantageously enables rapid, simple and no-touch testing of the fluid sample. The apparatus 2 is able to manufactured in a cost-effective manner which is comparable to existing apparatus. The apparatus 2 may be manufactured in a controlled environment, for example with a relative humidity of 11-15% and within a set temperature range of, for example, 19-23° C.

It is only necessary for a patient to hand the container with the liquid specimen to an authorised operator. After removal of the light-excluding cover, the authorised operator then only has to press the lid 12 in order to cause the pin 32 to pierce the openable means 16. The openable means 16 is in the form of a waterproof tab covering a central aperture 34 of the testing surface of the response chart 6. The container 4 is then inverted to allow the liquid specimen to flow into the lid 12. The container 4 is then returned to its normal upright position. The liquid specimen then drains back into the container 4. This draining of the liquid specimen back into the container 4 is aided by the lid 12 having a slight gradient towards the central aperture 34. Pooling of the liquid specimen on the response portions 18 may be avoided by having the response portions 18 raised, for example on stalks 36 or other formations.

The chromatographic time band 20 is made of paper with a known absorbency to the liquid specimen. Immersion of one end of the reagent strip 30 into the liquid specimen in the test chamber 14 allows the liquid specimen to track along the reagent strip 30 at a known speed. At specific points along the reagent strip 30, and specifically at twenty seconds, thirty seconds, forty seconds, sixty seconds and two minutes, there is a strip of reagent known to change colour in the presence of the liquid specimen. In the case of urine, the strip of reagent is known to change colour in the presence of urea. The result portions 24 are arranged in the illustrated circular manner and in relation to the chromatographic time band 20 such that reading is easy and it incorporates a timing element.

When the apparatus 2 has been used, the container 4 can be discarded into an appropriate waste disposal facility for incineration. It is not necessary for the container 4 to have been opened. This avoids the possibility of the authorised operator and the environment becoming contaminated by the urine under test, as occurs with the known method involving the use of a dip stick. Thus the apparatus 2 is able to be produced in a cost-effective manner, and it is able to be used in a faster, more convenient manner and with fewer steps than existing urine testing methods involving a dipstick. The risk of urine contamination is substantially reduced. A sink and a work surface are not required. The use of the chromatographic time band gives greater test accuracy.

Referring to FIGS. 1 and 2, it will be seen that the apparatus 2 is such that the response chart 6 is inside the container 4. It will also be seen that the result chart 8 is mounted on the outside of the container 4 by releasable securing means 38. Aligning means 40 are provided for aligning one of the result sectors 22 with one of the response portions 18 such that each one of the result sectors 22 has its own one of the response portions 18. In FIGS. 1 and 2, the releasable securing means 38 comprises the central aperture 26 in the result chart 8 and an upstanding portion 42 which is part of the container 4. The result chart 8 fits over the upstanding portion 42 and is a friction fit with respect to the upstanding portion 42.

In FIGS. 1 and 2, the aligning means 40 comprises a marking in the form of an arrow 44 and parallel lines 46 on the result chart 8, and a formation 48 on the upstanding portion 42. The upstanding portion 42 may be regarded as an upstanding lip on the container 4.

In FIGS. 8-14, similar parts as in previous Figures have been given the same reference numerals for ease of comparison and understanding.

Figures 8, 9:
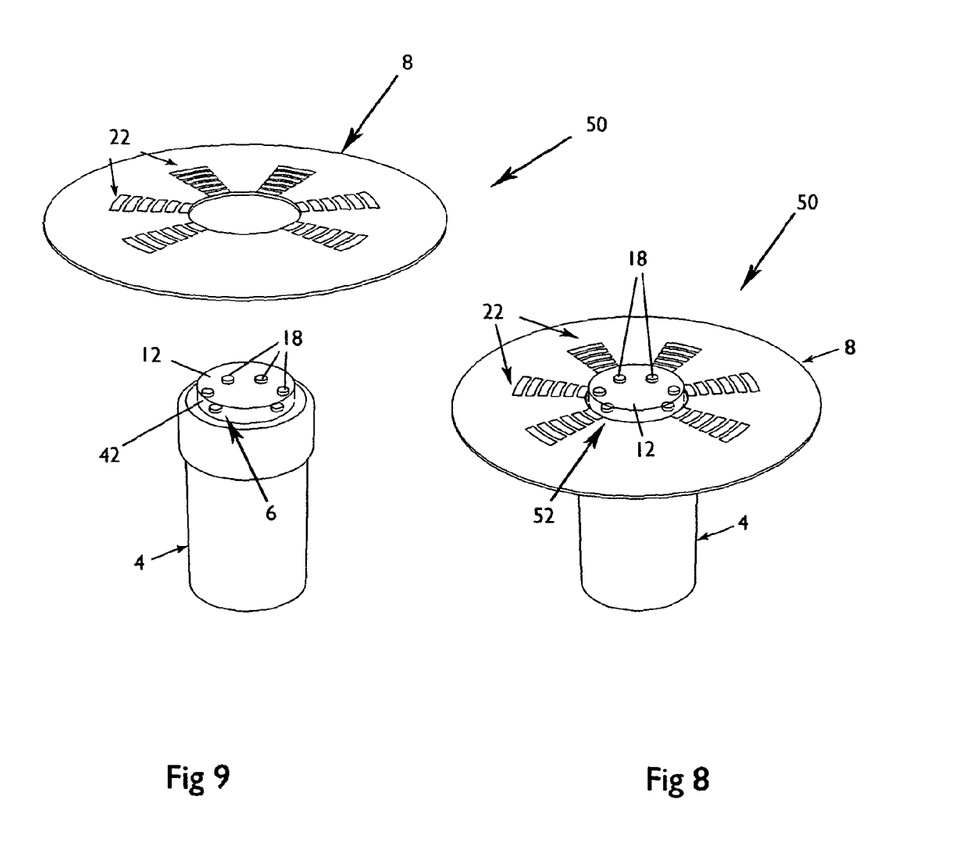
FIG. 8 is an isometric view from above and one side of second apparatus for testing a liquid specimen.
FIG. 9 is an exploded view of the second apparatus shown in FIG. 8.

In FIGS. 8 and 9, there is shown part of second apparatus 50. FIGS. 8 and 9 illustrate how the second apparatus 50 has releasable securing means 52 in the form of a central aperture 26 and an upstanding portion 42. FIG. 9 also illustrates how the response chart 6 comprising the response portions 18 is inside the lid 12 of the container 4.

Figure 10:
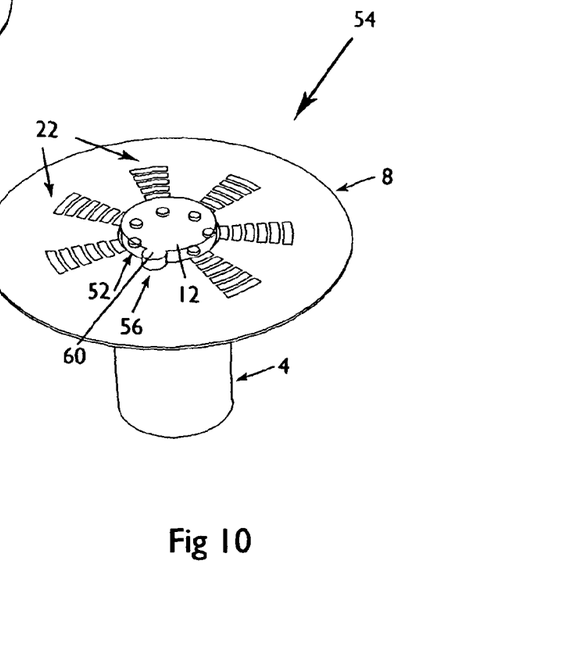
FIG. 10 is an isometric view from above and one side of third apparatus for testing a liquid specimen.
Figure 11:
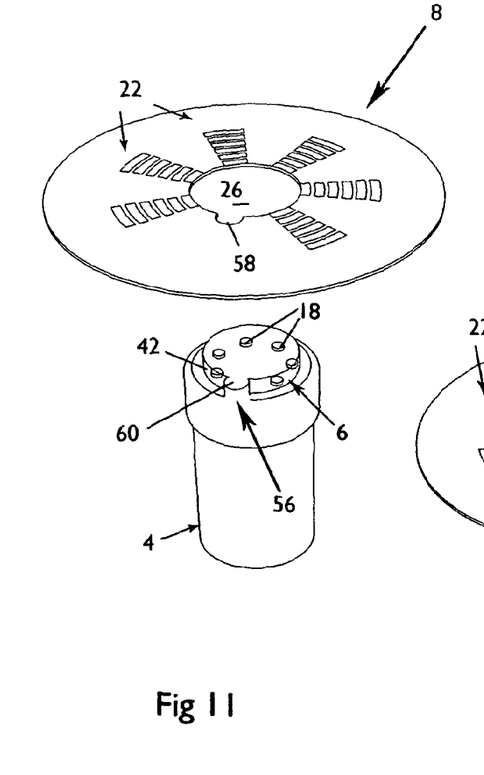
FIG. 11 is an exploded view of the third apparatus shown in FIG. 10.

FIGS. 10 and 11 show part of third apparatus 54. The apparatus 54 has releasable securing means 52 and aligning means 56. The aligning means 56 comprises a first part in the form of a notch 58 on the result chart 8, and a second part in the form of a protuberance 60 on the response chart 6 and therefore on the container 4. The protuberance 60 fits in the notch 58 in order to align the response portions 18 in the response chart 6 with the result sectors 22 in the result chart 8.

Figures 12, 13:
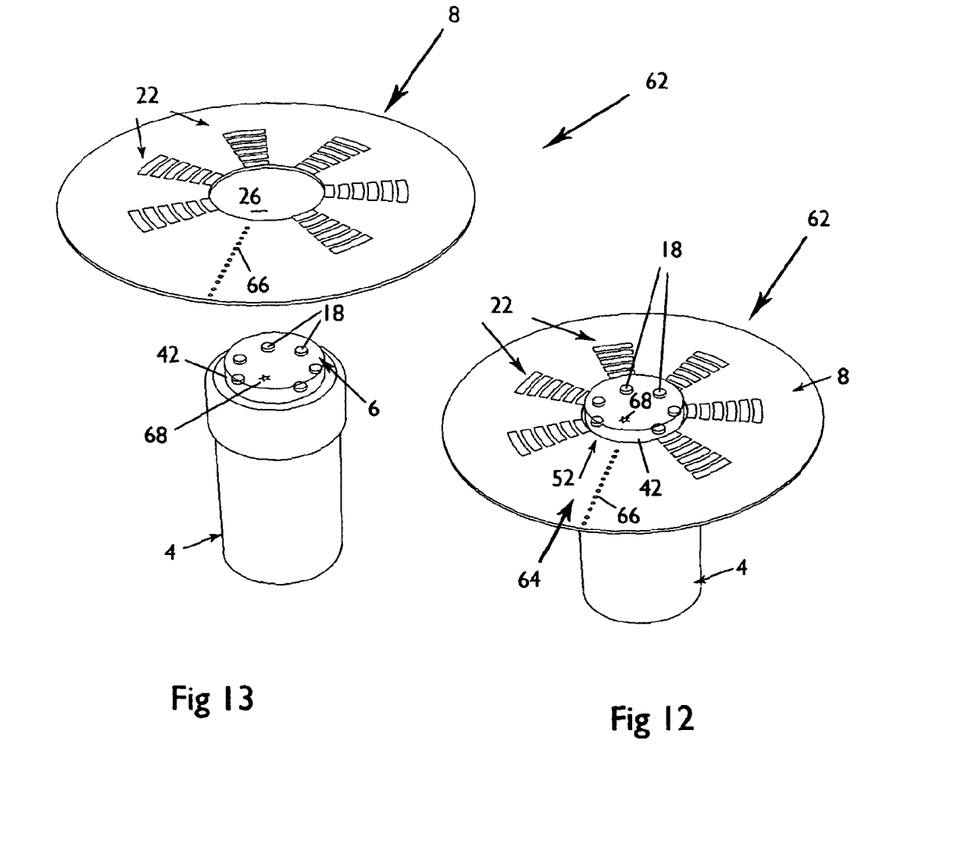
FIG. 12 is an isometric view from above and one side of fourth apparatus for testing a liquid specimen.
FIG. 13 is an exploded view of the fourth apparatus shown in FIG. 12.

FIGS. 12 and 13 show part of fourth apparatus 62 which is like the apparatus 54 except that the aligning means 56 has been replaced by aligning means 64. The aligning means 64 comprises a first part on the result chart 8 in the form of a line marking 66, and a second part on the container 4 in the form of a star marking 68.

Figures 14, 15:
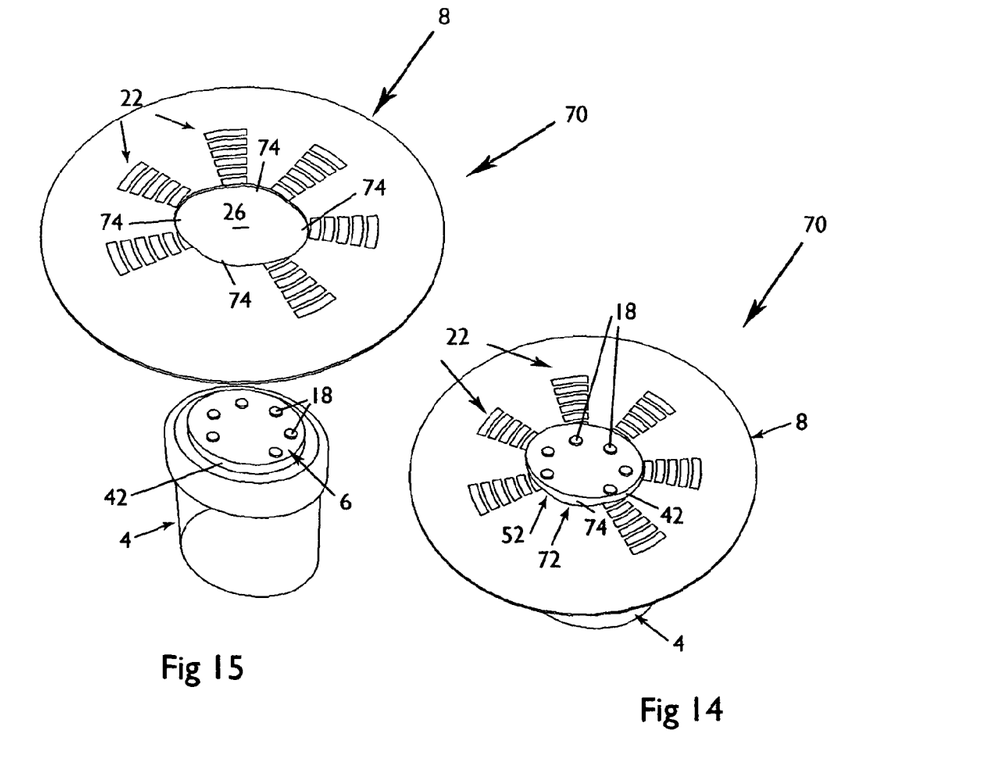
FIG. 14 is an isometric view from above and one side of fifth apparatus for testing a liquid specimen.
FIG. 15 is an exploded view of the fifth apparatus shown in FIG. 14.
Figure 16:
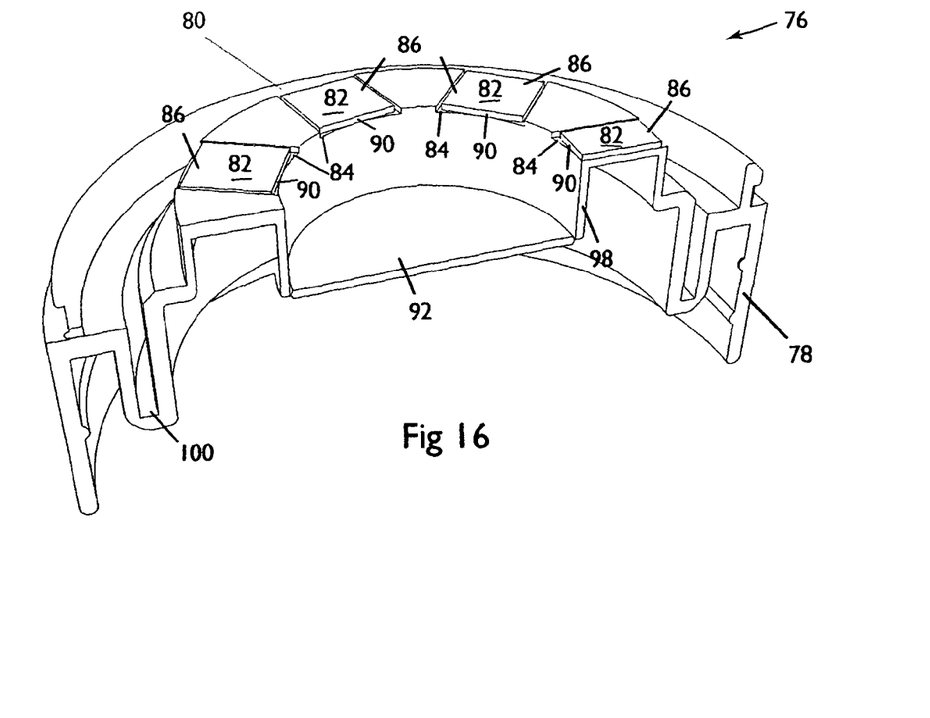
FIG. 16 shows a part of a container used in sixth apparatus of the present invention and without a lid.
Figure 17:
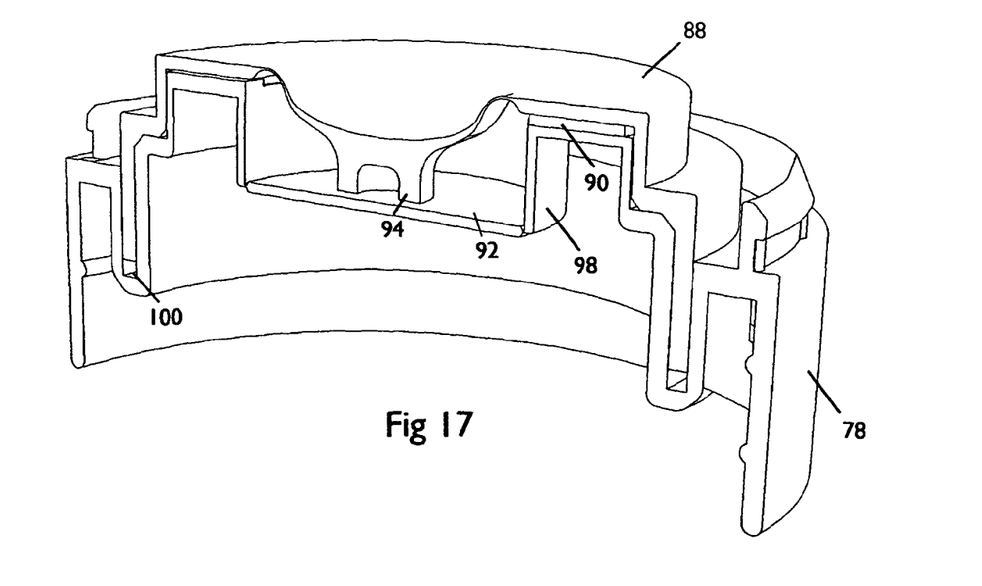
FIG. 17 shows the part of the container of FIG. 16 but with a lid and showing also openable means in a sealed condition.
Figure 18:
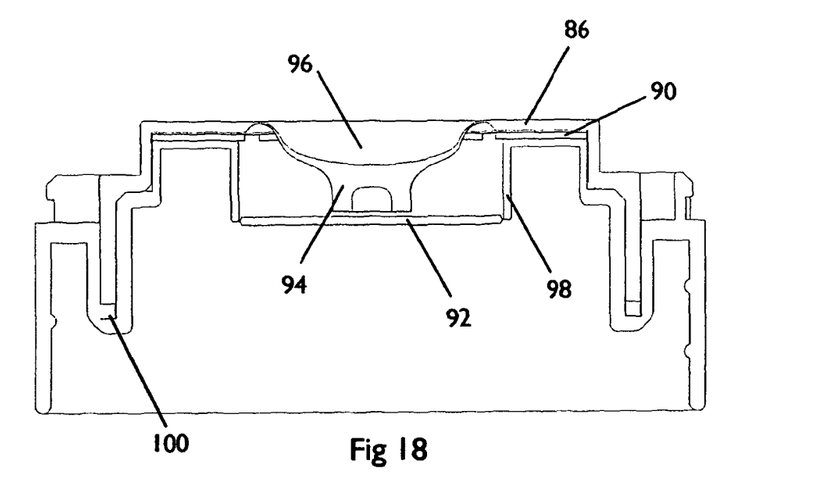
FIG. 18 is another view of the part of the container as shown in FIG. 17.
Figure 19:
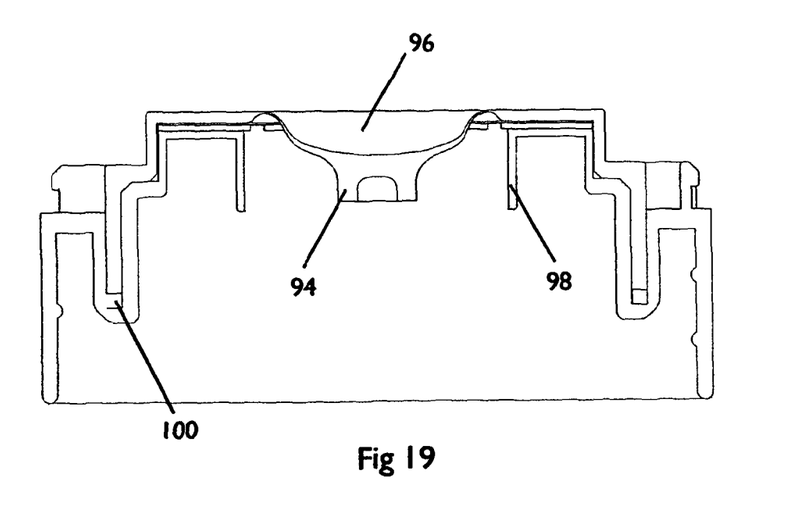
FIG. 19 is a view like FIG. 18 but shows the openable means having been opened.

FIGS. 14 and 15 show part of fifth apparatus 70 which is like the apparatus 54 except that the apparatus 70 has aligning means 72. The aligning means 72 is formed with the releasable securing means 52. More specifically, the aligning means 72 comprises the central aperture 26 but formed such that the central aperture 26 is an oval aperture 26 having peripheral portions 74 which extend outwardly with respect to the circular upstanding portion 42 and enable registration as shown in FIG. 14.

Referring now to FIGS. 16-19, there is shown part of sixth apparatus 76 of the present invention. More specifically, there is shown the upper part of a container 78 having a response chart 80 with response portions 82. The response portions 82 sit in recesses 84. As can best be appreciated from FIGS. 17 and 18, the majority of the response portions 82 constitute a first area 86 which is contacted by a lid 88. The first area 86 of each response portion 82 is thus in contact with the underside of the lid 88 and there is no gap between the top of the first area 86 and the underside of the lid 88. If the liquid specimen under test has a tendency to cause the underside of the lid 88 to mist up, then this is prevented because there is no gap between the first area 86 and the lid 88. The liquid specimen under test is still able to contact the response portions 82 because each response portion 82 has a second area 90 which is not in contact with the lid 88 and which is effectively an inner edge of each response portion 82. The second area 90 is contacted by the liquid specimen under test, which then soaks to the first area 86.

FIGS. 16-19 also show how the container 78 is able to be provided with openable means 92. The openable means 92 is in the form of a disc or bung. The openable means 92 is contacted by a formation 94 on the lid 88. When a recessed portion 96 is pressed inwardly, the openable means 92 is forced away from a retaining skirt portion 98 and the openable means 92 is thus opened.

As shown in FIGS. 16-19, the lid 88 fits in a groove 100 in a body part of the container 78.

Figure 20:
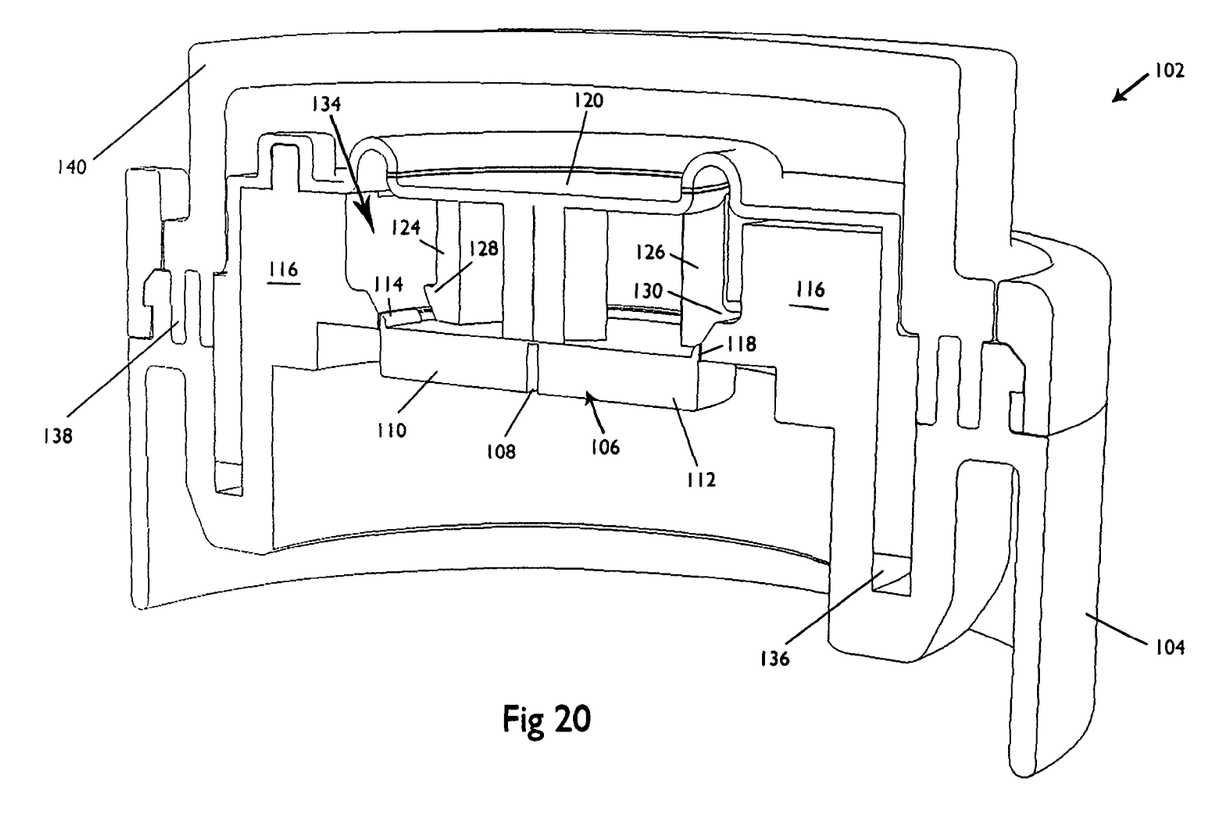
FIG. 20 is a view like FIG. 17 but shows part of a container used in seventh apparatus of the present invention and with openable means in a sealed condition.
Figure 21:
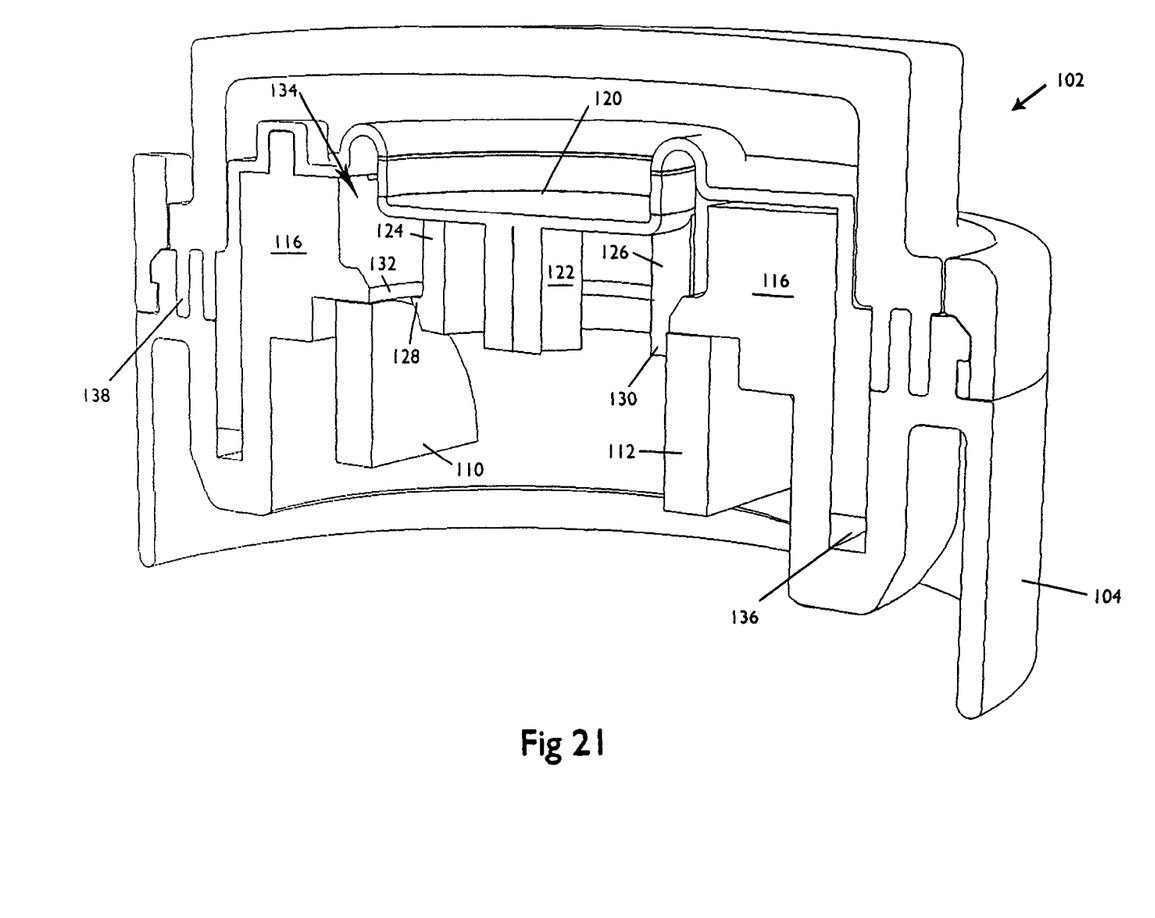
FIG. 21 is a view like FIG. 20 but shows the operable means having been opened.

Referring now to FIGS. 20 and 21, there is shown part of seventh apparatus 102 of the present invention. More specifically, there is shown the upper part of a container 104 having openable means 106. The openable means 106 has a groove 108 which divides the openable means 106 into two parts 110, 112. The part 110 is hinged by a hinge 114 to a part 116 of the container 104. Similarly, the part 112 is hinged by a hinge 118 to the part 116 of the container 104. Downward pressure on a platform part 120 causes a formation 122 to bear on the openable means 106 above the groove 108. This causes the part of the openable means 106 defining the bottom of the groove 108 to break and then the parts 110, 112 pivot about their respective hinges 114, 118 to the open position shown in FIG. 21.

The container 104 has a pair of hooked legs 124, 126 depending from the underside of the platform part 120. The hooked legs 124, 126 terminate in hooks 128, 130 respectively. When the formation 122 moves downwardly to open the openable means 106 as shown in FIG. 21, the hooks 128, 130 hook under a rim 132, and thereby bear on the parts 110, 112 to keep them open as shown in FIG. 21. As also shown in FIG. 21, the openable means 106 is in the form of a disc. The disc may be regarded as a frangible membrane. The holding of the parts 110, 112 in the open position by the hooks 128, 130 is advantageous in ensuring that the openable means 106 stays open and thereby allows the liquid specimen under test, for example urine, to flow easily into a test chamber 134.

FIGS. 20 and 21 also illustrate how the apparatus 102 includes a first labyrinth seal 136 for stopping the liquid specimen under test and also air from entering into the test chamber 134 before the openable means 106 is opened. FIGS. 20 and 21 further illustrate how the apparatus 102 is provided with a second labyrinth seal 138 for stopping light entering into the test chamber 134 before a light-preventing cover 140 is removed.

The apparatus 102 has two openable areas where ultraviolet light is excluded. The first area has the light-preventing cover 140 which may be plastics material or foil. The second area has the openable means 106 which may be a plastics bung or a foil. The means for excluding the ultraviolet light in the first and/or second area may be in the form of a plastics and foil membrane. The use of the light-preventing means may be advantageous if there is a problem with light, for example ultraviolet light, passing through the openable means such for example as the openable means 106. The light-preventing means may advantageously easily be broken. The exclusion of the light, for example the ultraviolet light, may be advantageous in cases where the light is likely to damage the response portions in the response chart.

The apparatus of the present invention, for example the apparatus 102 shown in FIGS. 20 and 21, may be provided with tamper-evident means that indicates if the light-preventing means has been broken. The tamper-evident means may be in the form of a seal. If the tamper-evident means has been broken, then a user of the apparatus of the present invention will be aware that the response portions may have been damaged by light, for example ultraviolet light.

In all the embodiments of the invention, it will be noticed that the releasable securing means secures the result chart 8 at a position which is level with or below the level of the response chart 6, whereby reading of the result chart 8 is facilitated and whereby the result chart 8 does not block light for reading of the response chart 6. Preferably, the result chart 8 is a transparent result chart 8, whereby the transparent result chart 8 does not block light for reading of the response chart 6.

The apparatus of the present invention, for example the apparatus 2, 50, may be used with standard known chemical reagents for testing one or more of glucose, bilirubin, ketones (acetoacetic acid), specific gravity, blood, pH, protein, urobilinogen, nitrites and leukocytes. Usually, a separate chemical reagent will be used for each test. Tests for other characteristics of the specimens may be conducted.

It is to be appreciated that the embodiments of the invention described above with reference to the accompanying drawings have been given by way of example only and that modifications may be effected. Thus, for example, the shape of the container 4, the lid 12, and the result chart 8 may be varied. Liquid specimens other than urine may be tested with an appropriate response chart 6 and a result chart 8. The apparatus 2, 50 may include light-preventing means, for example the cover 140, for preventing light from reaching the response portions 18 before the openable means has been opened and the light-preventing means removed, and thereby to prevent light-sensitive chemical reagents on the response portions 18 being adversely affected by the light. The apparatus 2, 50 may be packaged in a wide variety of ways, for example in a box of ten containers 4 with one result chart 8 for each ten containers 4. The apparatus may be packed in a box which is constructed and designed as a dispensing box. Other ratios of response charts to containers may be employed. The time band may be other than the chromatographic time band 20. The time band may be omitted from the apparatus of the invention if desired. Individual components shown in the drawings are not limited to use in their drawings and they may be used in other drawings and in all aspects of the invention.

The invention claimed is:

1. Apparatus for testing a liquid specimen, which apparatus comprises a container for the liquid specimen, a response chart which is operable in response to contact with the liquid specimen, and a result chart for use with the response chart, and the apparatus being such that:
   (i) the container comprises a body portion, a lid, a test chamber, and openable means which is adapted to be opened in order to allow the liquid specimen to pass from the body portion into the test chamber;
   (ii) the response chart comprises response portions which are contacted by the liquid specimen, which become differently coloured to indicate different characteristics present in the liquid specimen, and which are read at predetermined time intervals;
   (iii) the result chart comprises result sectors, each result sector is for indicating the result of a different test for the liquid specimen, and each result sector has a plurality of differently coloured result portions, and the different colours of the result portions in each result sector indicate different degrees of result for the test afforded by the result sector;
   (iv) the response chart is inside the test chamber;
   (v) the result chart is outside of the container; and
   (vi) the result chart has an aperture which receives a to part of the container, and a peripheral portion which extends transversely outwardly beyond the container and which contains the result sectors.

2. Apparatus according to claim 1 and including aligning means for aligning one of the result sectors with one of the response portions such that each one of the result sectors has its own one of the response portions.

3. Apparatus according to claim 1 in which the test chamber having the response chart therein is located on the inside of the lid of the container.

4. Apparatus according to claim 1 in which the response portions are arranged in a circle, and in which the result sectors are arranged in a circle and they extend radially outwardly with respect to the aperture.

5. Apparatus according to claim 1 in which the result chart is mounted on the outside of the container.

6. Apparatus according to claim 1 in which the result chart is a transparent result chart, whereby the transparent result chart does not block light for reading of the response chart.

7. Apparatus according to claim 1 in which the response portions in the response chart are rectangles.

8. Apparatus according to claim 1 in which the result portions in the result chart are ring segments.

9. Apparatus according to claim 1 in which the response portions in the response chart are such that they each comprise a first area which is in contact with the lid, and a second area which is not in contact with the lid.

10. Apparatus according to claim 1 in which each result portion in the result chart has a window portion through which the relevant response portion of the response chart can be viewed if the result chart is moved over the response chart, thereby to facilitate accurate colour matching of the response portion with its result portion.

11. Apparatus according to claim 1 and including light-preventing means for preventing light from prematurely reaching the response chart.

12. Apparatus according to claim 11 and including tamper-evident means for indicating if the light-preventing means has been damaged.

13. Apparatus according to claim 1 in which the openable means is a membrane or a foil.

14. Apparatus according to claim 1 and including a pin for piercing the openable means.

* * * * *